United States Patent
Springer et al.

(10) Patent No.: US 9,494,588 B2
(45) Date of Patent: Nov. 15, 2016

(54) GENE CODED FOR A MHC CLASS I MOLECULE, PLASMID, EXPRESSION SYSTEM PROTEIN, MULTIMER, REAGENT AND KIT TO ANALYZE A T CELL FREQUENCY

(75) Inventors: Sebastian Springer, Bremen (DE); Martin Zacharias, Garching (DE)

(73) Assignee: JACOBS UNIVERSITY BREMEN GGMBH, Bremen (DE)

( * ) Notice: Subject to any disclaimer, the term of this patent is extended or adjusted under 35 U.S.C. 154(b) by 127 days.

(21) Appl. No.: 13/583,933

(22) PCT Filed: Aug. 30, 2011

(86) PCT No.: PCT/IB2011/003373
§ 371 (c)(1),
(2), (4) Date: Jan. 25, 2013

(87) PCT Pub. No.: WO2013/030620
PCT Pub. Date: Mar. 7, 2013

(65) Prior Publication Data
US 2014/0162293 A1   Jun. 12, 2014

(51) Int. Cl.
C07K 16/28 (2006.01)
C07K 14/74 (2006.01)
A61K 39/00 (2006.01)
G01N 33/569 (2006.01)
C07K 14/47 (2006.01)

(52) U.S. Cl.
CPC ......... *G01N 33/56972* (2013.01); *C07K 14/47* (2013.01); *C07K 14/70539* (2013.01); *A61K 2039/605* (2013.01); *C07K 16/2833* (2013.01)

(58) Field of Classification Search
None
See application file for complete search history.

(56) References Cited

U.S. PATENT DOCUMENTS

| 5,286,632 A | 2/1994 | Jones |
| 5,451,512 A | 9/1995 | Apple et al. |
| 5,550,039 A | 8/1996 | Trachtenberg |
| 5,789,166 A | 8/1998 | Bauer et al. |
| 5,932,419 A | 8/1999 | Bauer et al. |
| 6,391,548 B1 | 5/2002 | Bauer et al. |
| 6,750,321 B1* | 6/2004 | Chen ............ A61K 38/30 530/317 |
| 7,132,265 B2 | 11/2006 | Bauer et al. |
| 7,176,004 B2 | 2/2007 | Bauer et al. |
| 2003/0007978 A1* | 1/2003 | Burrows ........ C07K 14/70539 424/185.1 |
| 2003/0228258 A1 | 12/2003 | Scheinberg et al. |
| 2006/0194267 A1* | 8/2006 | Vojdani .............. G01N 33/53 435/7.32 |

FOREIGN PATENT DOCUMENTS

DE   20 2010 003 498 U1   7/2011

OTHER PUBLICATIONS

Bjorkman et.al., (Nature 1987, 329(8): 506-512).*
Hansen et al (Curr. Prot. Immunol., 2009, Suppl. 87: 17.5.1-17.5.17).*
Godeau et al (J. Biol. Chem., 1992, 267(34): 24223-24229).*
Reference biology online (2016, world wide web at biology-online.org).*
"Human MHC class I histocompatibility antigen HLA-B (HLA-B-4803 allele) m-RNA, complete cds", GenBank U09912.1, .ncbi.nlm,nih.gov (May 20, 2000).
H. Cohen et al.: "In Vivo Expression of MHC Class I Genes Depends on the Presence of a Downstream Barrier Element", PLoS ONE, vol. 4, Issue 8, pp. 1-16 (Aug. 2008).
M. Sun et al.: "MHC class I multimers", Arthritis Research, vol. 3, No. 5, pp. 265-269 (Jul. 2, 2001).

* cited by examiner

*Primary Examiner* — Gerald R Ewoldt
*Assistant Examiner* — Marianne Dibrino
(74) *Attorney, Agent, or Firm* — Norman B. Thot

(57) ABSTRACT

A protein produced by an expression system that includes a nucleic acid sequence that encodes an MHC class I heavy chain. The MHC class I heavy chain comprises an alpha-1 helix and an alpha-2 helix. The nucleic acid sequence has a disulfide bridge formed between the alpha-1 helix and the alpha-2 helix in the MHC class I heavy chain. Amino acid 139 is substituted by a cysteine so as to provide Cys-139. Amino acid 84 is substituted by the cysteine so as to provide Cys-84 or amino acid 85 is substituted by the cysteine so as to provide Cys-85. The disulfide bridge is formed between the alpha-1 helix and the alpha-2 helix in the MHC class I heavy chain between Cys-139 and Cys-84 or between Cys-139 and Cys-85. The protein comprises an anchor element selected from a natural biotinylation sequence, a polyhistidine sequence, or a polyarginine sequence.

9 Claims, 1 Drawing Sheet

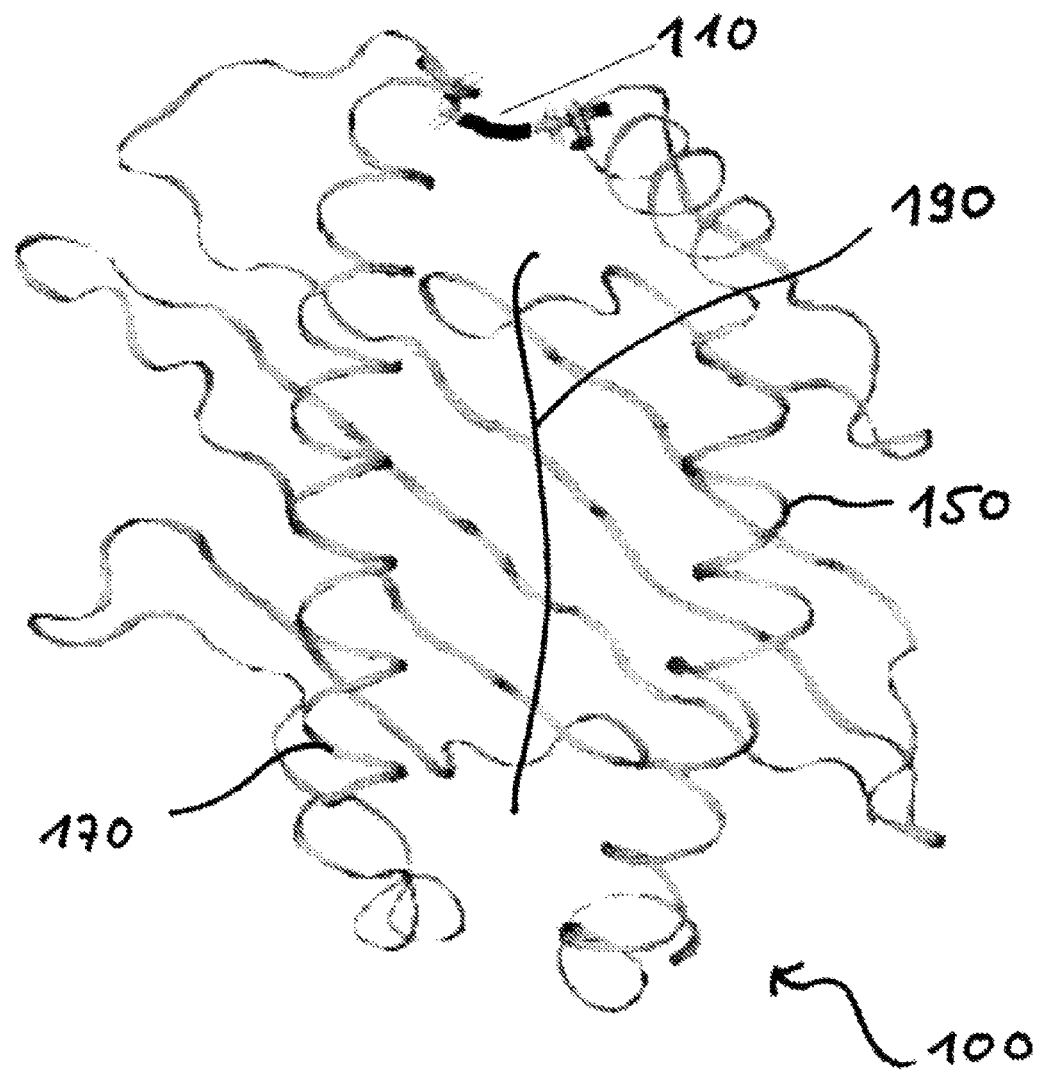

SEQUENCE LISTING

```
<160> NUMBER OF SEQ ID NOS: 8

<210> SEQ ID NO 1
<211> LENGTH: 1110
<212> TYPE: DNA
<213> ORGANISM: Murine
<220> FEATURE:
<221> NAME/KEY: gene
<222> LOCATION: (1)..(1110)

<400> SEQUENCE: 1
atggtaccgt gcacgctgct cctgctgttg gcggccgccc tggctccgac tcagacccgc      60
gcgggcccac actcgctgag gtatttcgtc accgccgtgt cccggcccgg cctcggggag     120
ccccggtaca tggaagtcgg ctacgtggac gacacgagt tcgtgcgctt cgacagcgac     180
gcggagaatc cgagatatga gccgcgggcg cggtggatgg agcaggaggg gcccgagtat     240
tgggagcggg agacacagaa agccaagggc aatgagcaga gtttccgagt ggacctgagg     300
accctgctcg gctactacaa ccagagcaag ggcggctctc acactattca ggtgatctct     360
ggctgtgaag tggggtccga cgggcgactc ctccgcgggt accagcagta cgcctacgac     420
ggctgcgatt acatcgccct gaacgaagac ctgaaaacgt ggacggcggc ggacatggcg     480
gcgctgatca ccaaacacaa gtgggagcag gctggtgaag cagagagact cagggcctac     540
ctggagggca cgtgcgtgga gtggctccgc agatacctga agaacgggaa cgcgacgctg     600
ctgcgcacag attccccaaa ggcccatgtg acccatcaca gcagacctga agataaagtc     660
accctgaggt gctgggccct gggcttctac cctgctgaca tcaccctgac ctggcagttg     720
aatggggagg agctgatcca ggacatggag cttgtggaga ccaggcctgc aggggatgga     780
accttccaga agtgggcatc tgtggtggtg cctcttggga aggagcagta ttacacatgc     840
catgtgtacc atcaggggct gcctgagccc ctcaccctga gatgggagcc tcctccatcc     900
actgtctcca acatggcgac cgttgctgtt ctggttgtcc ttggagctgc aatagtcact     960
ggagctgtgg tggcttttgt gatgaagatg agaaggagaa acacaggtgg aaaaggaggg    1020
gactatgctc tggctccagg ctcccagacc tctgatctgt ctctcccaga ttgtaaagtg    1080
atggttcatg accctcattc tctagcgtga                                     1110

<210> SEQ ID NO 2
```

```
<211> LENGTH: 1089
<212> TYPE: DNA
<213> ORGANISM: Homo sapiens
<220> FEATURE:
<221> NAME/KEY: gene
<222> LOCATION: (1)..(1089)

<400> SEQUENCE: 2
atgcgggtca cggcgccccg aaccctcctc ctgctgctct gggggggcagt ggccctgacc    60
gagacctggg ccggctccca ctccatgagg tatttctaca ccgccatgtc ccggcccggc   120
cgcggggagc cccgcttcat caccgtgggc tacgtggacg acacgctgtt cgtgaggttc   180
gacagcgacg ccacgagtcc gaggaaggag ccgcgggcgc catggataga gcaggagggg   240
ccggagtatt gggaccggga gacacagatc tccaagacca cacacagac ttaccgagag   300
aacctgcgca ccgcgctccg ctactacaac cagagcgagg ccgggtctca catcatccag   360
aggatgtacg gctgcgacgt ggggccggac gggcgcctcc tccgcgggta tgaccaggac   420
gcctacgacg gcaaggatta catcgccctg aacgaggacc tgagctcctg gaccgcggcg   480
gacaccgcgg ctcagatcac ccagcgcaag tgggaggcgg ccgtgtggc ggagcaggac   540
agagcctacc tggagggcct gtgcgtggag tcgctccgca gatacctgga aacgggaag   600
gagacgctgc agcgcgcgga ccccccaaag acacatgtga cccaccaccc catctctgac   660
catgaggtca ccctgaggtg ctgggccctg gcttctacc ctgcggagat cacactgacc   720
tggcagcggg atggcgagga ccaaactcag gacaccgagc ttgtggagac cagaccagca   780
ggagatagaa ccttccagaa gtgggcagct gtggtggtgc ttctggaga agagcagaga   840
tacacatgcc atgtacagca tgagggggctg ccgaagcccc tcaccctgag atgggagccg   900
tcttcccagt ccaccgtccc catcgtgggc attgttgctg gctggctgt cctagcagtt   960
gtggtcatcg gagctgtggt cgctgctgtg atgtgtagga ggaagagctc aggtggaaaa   1020
ggagggagct actctcaggc tgcgtgcagc gacagtgccc agggctctga tgtgtctctc   1080
acagcttga                                                         1089

<210> SEQ ID NO 3
<211> LENGTH: 13
<212> TYPE: PRT
<213> ORGANISM: Unknown
<220> FEATURE:
<223> OTHER INFORMATION: Biotinylation Sequence

<400> SEQUENCE: 3

Leu Ala Ala Ile Phe Glu Ala Gln Lys Ile Glu Trp Arg
1               5                   10

<210> SEQ ID NO 4
<211> LENGTH: 54
<212> TYPE: DNA
<213> ORGANISM: Unknown
<220> FEATURE:
<223> OTHER INFORMATION: Reverse Primer
<220> FEATURE:
<221> NAME/KEY: misc_feature
<222> LOCATION: (1)..(54)
<223> OTHER INFORMATION: Part of Reverse Primer

<400> SEQUENCE: 4
ttaacgatga ttccacacca ttttctgtgc atccagaata tgatgcaggg atcc          54

<210> SEQ ID NO 5
<211> LENGTH: 45
```

```
<212> TYPE: DNA
<213> ORGANISM: Unknown
<220> FEATURE:
<223> OTHER INFORMATION: Primer
<220> FEATURE:
<221> NAME/KEY: misc_feature
<222> LOCATION: (1)..(45)
<223> OTHER INFORMATION: Primer

<400> SEQUENCE: 5
tgaaaacgtg gacggcagct gacatgtgtg cgcagatcac ccgac         45

<210> SEQ ID NO 6
<211> LENGTH: 45
<212> TYPE: DNA
<213> ORGANISM: Unknown
<220> FEATURE:
<223> OTHER INFORMATION: Primer
<220> FEATURE:
<221> NAME/KEY: misc_feature
<222> LOCATION: (1)..(45)
<223> OTHER INFORMATION: Primer

<400> SEQUENCE: 6
gtcgggtgat ctgcgcacac atgtcagctg ccgtccacgt tttca         45

<210> SEQ ID NO 7
<211> LENGTH: 38
<212> TYPE: DNA
<213> ORGANISM: Unknown
<220> FEATURE:
<223> OTHER INFORMATION: Primer
<220> FEATURE:
<221> NAME/KEY: misc_feature
<222> LOCATION: (1)..(38)
<223> OTHER INFORMATION: Primer

<400> SEQUENCE: 7
gcctgaggaa cctcctaggc tactgcaacc agagcgcg               38

<210> SEQ ID NO 8
<211> LENGTH: 38
<212> TYPE: DNA
<213> ORGANISM: Unknown
<220> FEATURE:
<223> OTHER INFORMATION: Primer
<220> FEATURE:
<221> NAME/KEY: misc_feature
<222> LOCATION: (1)..(38)
<223> OTHER INFORMATION: Primer

<400> SEQUENCE: 8
cgcgctctgg ttgcagtagc ctaggaggtt cctcaggc               38
```

GENE CODED FOR A MHC CLASS I MOLECULE, PLASMID, EXPRESSION SYSTEM PROTEIN, MULTIMER, REAGENT AND KIT TO ANALYZE A T CELL FREQUENCY

CROSS REFERENCE TO PRIOR APPLICATIONS

This application is a U.S. National Phase application under 35 U.S.C. §371 of International Application No. PCT/IB2011/003373 filed on Aug. 30, 2011. PCT/IB2011/003373 was received by the International Bureau of WIPO on Aug. 22, 2012 from the Deutsches Patentamt Abteilung Informationsdienste with reference PCT/DE2011/001656. PCT/DE2011/001656 was filed as an International Application with the German Patent and Trademark Office on Aug. 30, 2011.

FIELD

The present invention relates to a gene coding for a MHC class I molecule, a plasmid and to an expression system, which have the gene, as well as proteins and multimers which are produced by means of the expression system.

SEQUENCE LISTING

The Sequence Listing associated with this application is filed in electronic form via EFS-Web and is hereby incorporated by reference into this specification in its entirety. The name of the text file containing the Sequence Listing is Sequence_Listing_21_JAN_2013. The size of the text file is 4,949 Bytes, and the text file was created on Jan. 21, 2013.

BACKGROUND

MHC class I molecules (Major Histocompatibility Complex Class I molecules) are transmembrane proteins of the cellular immune response which bind peptides from inside the cell, for example, from the cytosol or the lumen of the endocytic organelles, and present them to cytotoxic T-cells (CTL, cytotoxic T lymphocytes) at the cell surface. This is called antigen presentation.

The binding of a T-cell receptor of a CTL to a class I peptide complex of an antigen presenting cell (APC) leads (depending on the location of the reaction in the body, the type of APC (B-cell, dendritic cell, etc.) and the state of activation of the CTL) to the activation of the CTL and/or to the induction of cell death (apoptosis) of the APC by the CTL.

The immune response is effective because the CTL, which react with self-peptides (which are produced from the body's own proteins), are eliminated in the thymus. For this reason, the recognition of a peptide by the CTL implies that the APC is producing foreign proteins which stem from viruses or intracellular parasites (bacteria, protozoa); the overproduction of endogenous peptides in malignant degenerate tumor cells can also lead to recognition reactions. Almost all the proteins contained in the cell break down into peptides at the end of their lifecycle, which then bind to MHC class I molecules in the reticulum (an organelle inside the cell surrounded by a membrane); subsequently, the complex consisting of the peptide and the MHC class I molecule is transported to the surface of the cell and is available there for recognition by CTL. If, due to a tumorigenic malignant degeneration, novel or mutated proteins are produced, or if, due to a viral infection, viral proteins are produced from the genetic material of the virus, these "novel" proteins are also broken down into peptides, which are then presented at the surface of the cell in the complex with MHC class I molecules. These "novel" peptides are different from the cell's own peptides and trigger recognition by the CTL.

Presentation by MHC class I molecules also plays a role in allergic reactions, transplant rejection and a number of auto-immune diseases such a multiple sclerosis and rheumatoid arthritis.

Examining the immune responses that are mediated by MHC class I molecules often requires detecting CTL which react with at certain class I peptide complex (epitope). Reactions to a single immunodominant epitope often account for 10-20% of the entire T-cell population in an organism and observing the CTL frequency thus allows for a precise observation of the immune response (and, for example, of the success or failure of a therapy). For this reason, reagents that can identify CTL, which recognize a certain selected epitope, are indispensable.

In order to detect such epitope-specific CTL, recombinant MHC class I molecules, which are produced in bacteria and are available as insoluble inclusion bodies, have until now been used by first denaturing them in a solution of a chaotropic agent. The chaotrope is then removed (for example, by renaturation and refolding) in the presence of the desired peptide, and the peptide class I complex is separated from the unfolded protein by means of gel filtration chromatography. Since the low affinity of a single class I peptide complex with a single T-cell receptor does not lead to a strong bond, multimers of class I-peptide-complexes are used, which, due to the avidity effect, bind to the T-cell receptors of a T-cell strongly enough to allow for a durable bond. Such multimers are obtained, for example, by streptavidin-mediated tetramerization of biotinylated class I peptide complexes (class I tetramers) or by pentamerization by self-assembling coiled coil domain (class I pentamers).

Class I multimers are generally marked with fluorescent colorants which allow them to be detected by a microscope or by flow cytometry. Epitope-specific CTL can thus be directly colored.

Other uses of recombinant class I peptide complexes are:
- In vitro—Selection and expansion of monospecific T-cells for reinfusion in cancer and viral diseases. (The selection can occur by means of cytofluorometry (flow cytometry) or, for increased throughput, in microarrays).
- Ex vivo—Isolation and expansion of CTL for adoptive therapy after allogeneic stem cell transplantation.
- Ex vivo—Removal of alloreactive T-cells after transplantation of peripheral stem cells. The removal of autoreactive T-cells, which cause type I diabetes, arthritis and other autoimmune diseases, is also interesting, as has already been described regarding MHC class II reagents. The use of isotope-marked multimers is described in US 2003/0228258 A1.

The production of recombinant class I peptide complexes is complex and expensive. On the one hand, there are several thousand MHC class I allotypes, of which however, five alleles of HLA-A cover about 50% of the world population. Mainly, however, a new multimer must be produced for each peptide that is to be examined as an epitope so that new multimers, which must be specifically produced, are required for each patient or for each experiment.

It would be simpler to produce the multimers without the peptides and to subsequently add the respectively-required peptides as required, but this has not been possible so far because refolding the class I molecules without the peptide is extremely inefficient. A remedy has previously been described. A light-sensitive peptide was used which breaks down under UV radiation or periodate treatment, and can then be replaced by adding a peptide.

This method, however, remains expensive and does not function with all peptides or class I molecules.

SUMMARY

An aspect of the present invention is to improve the disadvantages of the prior art.

In an embodiment, the present invention provides a gene which is coded for a MHC class I molecule. The MHC class I molecule comprises an ALPHA-1 helix and an ALPHA-2 helix. The gene is coded so that a bond is formed between the ALPHA-1 helix and the ALPHA-2 helix in the MHC class I molecule.A.

BRIEF DESCRIPTION OF THE DRAWINGS

The present invention is described in greater detail below on the basis of embodiments and of the drawing in which:

FIG. 1 shows a schematic spatial representation of a MHC class I molecule with an inserted peptide.

DETAILED DESCRIPTION

The following terms must be explained:

A "gene" is a sequence of nucleotides that can be used to program cells (more specifically, bacteria, yeast cells, insect cells or mammalian cells) or a cell free expression system so that the heavy chain of a MHC class I molecule is synthesized. Examples of such genes are the gene sequence of the murine MHC class I molecule H-2Kb as set forth in SEQ ID NO: 1

```
(atggtaccgtgcacgctgctcctgctgttggcggccgccctggctccga
ctcagacccgcgcgggcccacactcgctgaggtatttcgtcaccgccgtg
tcccggcccggcctcggggagcccggtacatggaagtcggctacgtgga
cgacacggagttcgtgcgcttcgacagcgacgcggagaatccgagatatg
agccgcgggcgcggtggatggagcaggaggggcccgagtattgggagcgg
gagacacagaaagccaagggcaatgagcagagtttccgagtggacctgag
gaccctgctcggctactacaaccagagcaagggcggctctcacactattc
aggtgatctctggctgtgaagtggggtccgacgggcgactcctccgcggg
taccagcagtacgcctacgacggctgcgattacatcgccctgaacgaaga
cctgaaaacgtggacggcggcggacatggcggcgctgatcaccaaacaca
agtgggagcaggctggtgaagcagagagactcagggcctacctggagggc
acgtgcgtggagtggctccgcagatacctgaagaacgggaacgcgacgct
gctgcgcacagattccccaaaggcccatgtgacccatcacagcagacctg
aagataaagtcaccctgaggtgctgggccctgggcttctaccctgctgac
atcaccctgacctggcagttgaatgggaggagctgatccaggacatgga
gcttgtggagaccaggcctgcaggggatggaaccttccagaagtgggcat
ctgtggtggtgcctcttgggaaggagcagtattacacatgccatgtgtac
catcaggggctgcctgagcccctcaccctgagatgggagcctcctccatc
cactgtctccaacatggcgaccgttgctgttctggttgtccttggagctg
caatagtcactggagctgtggtggcttttgtgatgaagatgagaaggaga
aacacaggtggaaaaggaggggactatgctctggctccaggctcccagac
ctctgatctgtctctcccagattgtaaagtgatggttcatgaccctcatt
ctctagcgtga)
``` and the gene sequence of the human MHC class 1 molecule HLA-B*4402 as set forth in SEQ ID NO: 2

```
(ATGCGGGTCACGGCGCCCCGAACCCTCCTCCTGCTGCTCTGGGGGGC
AGTGGCCCTGACCGAGACCTGGGCCGGCTCCCACTCCATGAGGTATTT
CTACACCGCCATGTCCCGGCCCGGCCGCGGGGAGCCCCGCTTCATCAC
CGTGGGCTACGTGGACGACACGCTGTTCGTGAGGTTCGACAGCGACGC
CACGAGTCCGAGGAAGGAGCCGCGGGCGCCATGGATAGAGCAGGAGGG
GCCGGAGTATTGGGACCGGGAGACACAGATCTCCAAGACCAACACACA
GACTTACCGAGAGAACCTGCGCACCGCGCTCCGCTACTACAACCAGAG
CGAGGCCGGGTCTCACATCATCCAGAGGATGTACGGCTGCGACGTGGG
GCCGGACGGGCGCCTCCTCCGCGGGTATGACCAGGACGCCTACGACGG
CAAGGATTACATCGCCCTGAACGAGGACCTGAGCTCCTGGACCGCGGC
GGACACCGCGGCTCAGATCACCCAGCGCAAGTGGGAGGCGGCCCGTGT
GGCGGAGCAGGACAGAGCCTACCTGGAGGGCCTGTGCGTGGAGTCGCT
CCGCAGATACCTGGAGAACGGGAAGGAGACGCTGCAGCGCGCGGACCC
CCCAAAGACACATGTGACCCACCACCCCATCTCTGACCATGAGGTCAC
CCTGAGGTGCTGGGCCCTGGGCTTCTACCCTGCGGAGATCACACTGAC
CTGGCAGCGGGATGGCGAGGACCAAACTCAGGACACCGAGCTTGTGGA
GACCAGACCAGCAGGAGATAGAACCTTCCAGAAGTGGGCAGCTGTGGT
GGTGCCTTCTGGAGAAGAGCAGAGATACACATGCCATGTACAGCATGA
GGGGCTGCCGAAGCCCCTCACCCTGAGATGGGAGCCGTCTTCCCAGTC
CACCGTCCCCATCGTGGGCATTGTTGCTGGCCTGGCTGTCCTAGCAGT
TGTGGTCATCGGAGCTGTGGTCGCTGCTGTGATGTGTAGGAGGAAGAG
CTCAGGTGGAAAAGGAGGGAGCTACTCTCAGGCTGCGTGCAGCGACAG
TGCCCAGGGCTCTGATGTGTCTCTCACAGCTTGA).
```

An "MHC class I molecule" is a major histocompatibility complex class I molecule which are transmembrane proteins of cellular immune response. These bind peptides from inside the cell, for example, from the cytosol or the lumen of the endocytic organelles. They also present an antigen presentation to the cytotoxic T-cells at the surface of the cell. In addition to actual MHC class I molecules, the term "MHC class I molecule" comprises similar molecules that are coded in the MHC and also bind peptides, such as, for example, HLA-E and HLA-G.

This "antigen presentation" is the display (by the antigen-presenting cell) of a complex consisting of the MHC class I molecule and the peptide at the surface of the cell for recognition by the T-cell receptor of a CTL, as well as the cellular processes in the antigen-presenting cell which directly lead thereto, for example, the breakdown (proteolysis) of cellular proteins, the transport of the produced peptides into the endoplasmic reticulum (a compartment inside the cell surrounded by a membrane), the binding of the peptides to the class I molecule, the transport of the class I-peptide complex to the surface of the cell.

The "ALPHA-1 helix" and the "ALPHA-2 helix" are helix-type structures of the MHC class I molecule which are disposed substantially across from each other in the molecule and between which the binding site of the peptide is located.

The "bond" can more specifically be designed as a covalent bond.

In an embodiment of the present invention, the distance between the ALPHA-1 helix and the ALPHA-2 helix amounts to between 2 angstrom and 10 angstrom, more specifically, between 2 angstrom and 5 angstrom, which span the bond.

It can thus be provided that the ALPHA-1 helix and the ALPHA-2 helix are coupled to each other by way of the formed bond. It can thereby be advantageous if the distance is as small as possible.

In order to provide the greatest possible stability of the bonded structure and simultaneously allow for a production of the bonded class I molecule in cells, the bond can be formed as a disulfide bridge.

As an alternative to the disulfide bridge, bridges can also be formed by attaching amino acids on opposing sites of the ALPHA-1 and the ALPHA-2 helix with such side chains that have opposite charges, more specifically, negatively charged amino acids (aspartate, glutamate) on the one helix and positively charged amino acids (histidine, arginine, lysine) on the other helix in such a manner that the opposite charges attract each other electrostatically.

In an embodiment of the present invention, the molecule has a placeholder for a peptide between the ALPHA-1 helix, and the ALPHA-2 helix and the bond keeps the placeholder free so that the peptide is insertable into the placeholder.

The peptides specified herein are more specifically commercially available peptides that are provided depending on the application, such as, for example, the specific disease that has to be examined.

In an embodiment, the present invention provides a plasmid which has a gene described above. A plasmid can thus be provided that implements a transcription of the gene.

In order to provide a protein, an embodiment of the present invention provides an expression system having the gene described above.

In an embodiment of the present invention, the expression system has a bacteria cell, more specifically an *escherichia coli* cell, a yeast cell, more specifically, a *saccharomyces cerevisiae* cell, an insect cell, more specifically a *spodoptera frugiperda* cell, a mammalian cell, more specifically CHO-cell, wherein CHO refers to Chinese hamster ovary, a cell free expression system, more specifically, as a reticulocyte lysate.

In order to obtain a maximum yield, the expression system has several cells, more specifically, a number of cells in the order of $10^6$ cells.

In an embodiment, the present invention provides a protein which has been produced by using the expression system described above.

In order, for example, to determine a specific T-cell concentration in a sample, a marker can be disposed on the protein, the marker being, more specifically, a fluorescent colorant. Simple methods for identification are thus provided.

In an embodiment of the present invention, the protein has an anchor element.

This anchor element is, more specifically, a biotin molecule that is attached to the protein either by a natural biotinylation sequence that is genetically coded in the gene, and a biotinylated enzyme, more specifically BirA, or by chemical methods, more specifically, the use of a N-hydroxysuccinimide derivative of biotin; or a polyhistidine or polyarginine sequence, more specifically, a hexahistidine sequence that is genetically coded in the gene.

In order to use the avidity effect, the an embodiment of the present invention provides a multimer, more specifically, a tetramer and/or a pentamer, which has at least two proteins, at least one protein being a previously-described protein.

In an embodiment of the present invention, a marker is disposed on the multimer, the marker being, more specifically, a fluorescent colorant. This provides a simple possibility for detecting the T-cell concentration.

In order to get the multimer back by filtration or chromatography, the multimer can have an anchor element. In addition, just as with the anchor elements for the peptides, other molecules can be coupled to the multimer or the peptide via these anchor elements in order to influence physical, chemical or mechanical properties of the multimer or the peptide.

In an embodiment, the present invention provides a reagent, more specifically, for diagnostic purposes, comprising a previously-described protein or a previously-described multimer, and a peptide, more specifically, a commercially available peptide. A reagent can thus be provided by which one can control which specific T-cell chip is analyzable. A reception molecule has also been created by the multimer and the protein in which the peptide is insertable.

In an embodiment, in order to provide efficient analysis with respect to a T-cell concentration in medical or clinical laboratories, the present invention provides a kit for analyzing a T-cell frequency comprising a first storage means with a previously-described protein and/or a previously-described multimer and second storage means with a peptide, wherein the contents of the storage means are adapted to be brought together, more specifically, manually. In this case, the peptide can also be a commercially available peptide.

The kit can also provide a series of different peptide selections as well as MHC class I molecules with different alleles.

In an embodiment, the present invention provides a method for frequency analysis of T-cells, the method comprising the following steps:
 bringing together a previously-described protein and/or a previously-described multimer with a peptide, so that a reagent is formed,
 bringing together the reagent with a cell sample, so that the reagent forms a complex with specific elements of the cell sample.

The cell samples can thereby more specifically include blood samples of humans, animals, more specifically, from mammals to cartilaginous fishes.

In this context, forming a complex means the specific bonding of the reagent through interactions between the atomic elements of the reagent and of the cell sample, more specifically, ionic bonds, hydrophobic interactions and hydrogen bridges.

In an embodiment of the method of the present invention, the marker is detected after bringing together the reagent and the cell sample. The detection of the marker can thereby occur amongst others by means of flow cytometry and microscopy.

In order to obtain a quick and effective analysis result, the cell sample can be purified before bringing together the reagent and the cell sample, the purification occurring more specifically by way of a density gradient centrifugation.

In order to determine the different variants of the MHC class I molecules present in the sample, a determination of the MHC class I molecules can first occur, wherein, more specifically, alleles of the MHC class I molecules are determined. This determination occurs, more specifically, by determining the gene sequences for MHC class I molecules by polymerase chain reaction, more specifically as described in U.S. Pat. No. 5,451,512 and U.S. Pat. No. 5,550,039.

In order to obtain the T-cells as a result of a separation from a cell sample, an embodiment of the present invention provides a method for separating T-cells from a cell sample, comprising the following steps:

bringing together a previously-described peptide and/or a previously-described multimer with a peptide, so that a reagent is formed, bringing together the reagent with a cell sample, so that the reagent forms a complex with specific elements of the cell sample, separating the complex, more specifically, by means of a chromatographic method.

The reagent and the cell sample correspond to the previously-described definitions, wherein, after implementing this method, the separated T-cells resulting from the separation process as well as the rest of the cell sample remaining from the previously provided cell sample are available.

In an embodiment of the method of the present invention, the complex has an anchor element and the separation occurs while using the anchor element. The retention times can thus be influenced.

In an embodiment, the present invention provides a dialysis machine which is set up so that the previously-described separation result or the previously-described rest is made available.

In an embodiment, the present invention provides a novel mutation in MHC class I molecules 100 that has not yet been described in the literature. It consists in the modification of the amino acids 139 (usually alanine) on the one hand and either 84 or 85 (usually tyrosine) on the other hand. These amino acids are mutated into cysteines by modifying the gene sequence.

Thereby, when folding the protein, a disulfide bridge 110 is formed between Cys-139 and Cys-84 and/or Cys-85. This disulfide bridge 110 has a stabilizing effect on the ALPHA-1 helix 170 and the ALPHA-2 helix 150 so that no peptide 190 is required for refolding the protein in vitro, and the peptide free class I molecule remains stable in the solution.

Class I oligomers without peptides can be produced and sold in this manner. When the oligomers are to be used, the peptide can then be directly added and a class I oligomer reagent with a corresponding peptide is then obtained that is ready for use. The specificity of these disulfide oligomers for T-cell receptors is identical to the specificity of the wild type oligomers.

The present invention extends to MHC class I alleles that are coded in the gene loci for HLA-A, HLA-B and HLA-C. It also extends to molecules similar to class I molecules that are coded in the MHC and also bind peptides, i.e., HLA-E and HLA-G.

The following applications can be implemented with the present invention: tetramers, pentamers, other oligomers for coloring specific T-cells; MHC-oligomers for isolating CTL of determined specificities; immobilization of the MHC-monomers or oligomers on solid bodies (capsules or particles in the micro or nanometer size range) for the purpose of specific stimulation of the immune response.

Description of the Production of a MHC Class I Tetramer

1) Mutagenesis a) A polymerase chain reaction (PCR) is implemented by a class I expression plasmid for attaching the biotinylation sequence LAAIFEAQKIEWR to the C-terminal of the recombinant protein. The forward primer has the sequence 5' x-y 3', x representing the cutting sequence of a restriction enzyme and y the beginning of the gene of the class I molecule (20 base pairs). The reverse primer (SEQ ID NO: 4) has the sequence 5' e-TTAACGATGATTCCACACCATTTTCTGTG-CATCCAGAATATGATGCAG GGATCC-f 3', e representing the cutting sequence of the restriction enzyme and f representing a sequence that is complementary to the end of the gene of the class I molecule but does not contain the stop codon.

b) The PCR product is cloned in an expression vector that contains a T7 promoter, more specifically, by cutting the ends of the PCR product with restriction enzymes and cutting the ends of the expression vector with restriction enzymes, which generate heel sequences that match the ends of the PCR product and by subsequent ligation of the PCR product into the expression vector by means of the ligase enzyme; or by cloning the PCR product into an expression vector by means of a commercially available PCR cloning kit, more specifically a TOPO® TA kit by the company Invitrogen, or a CloneJet™ Kit of the company Fermentas. The sequence of the product is then verified by sequencing.

c) In order to produce the disulfide mutants, the amino acid 139 is first mutated into a cysteine. This occurs by so-called QuikChange™ mutagenesis (Kit, Statagene; U.S. Pat. No. 5,789,166, U.S. Pat. No. 5,932,419, U.S. Pat. No. 6,391,548, U.S. Pat. No. 7,132,265, U.S. Pat. No. 7,176,004, U.S. Pat. No. 5,286,632). The expression plasmid is thereby amplified by two overlapping opposing primers (more specifically, the primers 5'-tgaaaacgtggacggcagctgacatgtgtgcgcagatcacccgac-3' (SEQ ID NO: 5) and 3'-acttttgcacctgccgtcgactgtaca-cacgcgtctagtgggctg-5' (the reverse of SEQ ID NO: 6) for the murine MHC class I molecule H-2D$^b$, which deviate from the original gene sequence according to the desired mutation at the site of the desired mutation, by means of a polymerase chain reaction. The plasmid with the original sequence remaining in the reaction mixture is broken down by means of the restriction enzyme Dpn1 and the reaction product is transformed into competent *E. coli* cells, more specifically, by production of competent cells by treatment of *E. coli* cells with dimethylsulfoxide or with calcium chloride, incubation of the treated cells with the expression plasmid and selection of the cells thus transformed on agar plates into which the antibiotic is added, which is catabolized by the enzyme that is coded by the resistance gene present on the expression plasmid. The sequence of the product is then verified by sequencing.

d) As a second step, either the amino acid 84 or the amino acid 85 is mutated into a cysteine. This occurs by so-called QuikChange™ mutagenesis (Kit, Statagene; U.S. Pat. No. 5,789,166, U.S. Pat. No. 5,932,419, U.S. Pat. No. 6,391,548, U.S. Pat. No. 7,132,265, U.S. Pat. No. 7,176,004, U.S. Pat. No. 5,286,632). The expression plasmid is thereby amplified by two overlapping opposing primers (more specifically the primers 5'-gc-ctgaggaacctcctaggctactgcaaccagagcgcg-3' (SEQ ID NO: 7) and 5'-cgcgctctggttgcagtagcctaggaggttcctcaggc-3' (SEQ ID NO: 8) for the murine MHC class I molecule H-2D$^b$ and for the mutation at position 85, which deviate from the original gene sequence according to the desired mutation at the site of the desired mutation, by means of a polymerase chain reaction. The plasmid with the original sequence remaining in the reaction mixture is broken down by means of the restriction enzyme Dpn1 and the reaction product is transformed into competent *E. coli* cells, more specifically, by production of competent cells by treatment of *E. coli* cells with dimethylsulfoxide or with calcium chloride, incubation of the treated cells with the expression plasmid and selection of the cells thus transformed on agar plates into which the antibiotic is added, which is catabolized by the enzyme that is coded by the resistance gene present on the expression plasmid. The sequence of the product is then verified by sequencing.

2) Production of the Expression Strain
   a) The expression plasmid is transformed into an *E. coli* expression strain (for example, BL21DE3(pLysS)), more specifically, by producing competent cells by treatment of *E. coli* cells with dimethylsulfoxide or with calcium chloride, incubation of the treated cells with the expression plasmid and selection of the cells thus transformed on agar plates into which the antibiotic is added, which is catabolized by the enzyme that is coded by the resistance gene present on the expression plasmid.
   b) The expression strain is frozen as a liquid culture with 20% glycerol and is storable for several years at −80° C.

3) Production of the Class I Protein
   a) 20 ml LB-medium with a corresponding amount of antibiotics (for example 100 μg/ml of Ampicilin) are inoculated with 100 μl of a preparatory culture of an expression strain of *Escherichia coli* that carries a plasmid with a class I gene (disulfide mutants) and are bred over night to a stationary phase at 37° C. in a shaking incubator.
   b) The culture is centrifuged (3000×g, 10 minutes, 25° C.), the supernatant is discarded and the sediment (cells) are used for inoculating a 1 liter culture of the same medium. The culture is bred in a shaking incubator at 37° C. until an extinction of 0.4-0.5 with 600 nm wavelength and a cuvette with a diameter of 1 cm is reached, which is measured with a spectrophotometer (ThermoSpectronic Genesys 10 UV).
   c) Isopropyl-β-D-1-thiogalactopyranoside (IPTG) is added to the culture with a final concentration of 0.5 mM, and the culture is then bred in the same conditions until an extinction of 1.0 with 600 nm wavelength and a cuvette diameter of 1 cm is reached, which is measured with a spectrophotometer (ThermoSpectronic Genesys 10 UV).
   d) The culture is centrifuged (13 000×g, 10 minutes, 25° C.), the supernatant is discarded and the sediment is resuspended in a 20 ml saccharose solution (25 Weight % saccharose, 1 mM ethylenediaminetetraacetic acid (EDTA), 1 mM phenylmethylsulfonyl fluoride (PMSF), 10 mM Tris(hydroxymethyl)aminomethane (Tris), pH 8.0). This suspension is transferred into a 50 ml centrifuge tube and frozen in the freezer.
   e) Cell lysis: The centrifuge tube with the cell suspension is thawed in a 30° C. water bath under shaking conditions. After thawing, the subsequent work is carried out on ice or in the cold room.
   f) Fragmentation of the DNA: The suspension is treated with the probe of an ultrasound machine until it is no longer visibly viscous.
   g) The suspension is centrifuged (40000×g, 15 minutes, 4° C.), the supernatant is discarded and the sediment is resuspended in a 20 ml detergent buffer by ultrasound treatment (25 Weight % saccharose, 1 Vol.-% Triton X-100, 5 mM EDTA, 2 mM DTT, 50 mM Tris, pH 8.0).
   h) The suspension is centrifuged (40000×g, 15 minutes, 4° C.), the supernatant is discarded and the sediment is resuspended in a 20 mL urea buffer by ultrasound treatment (2 M NaCl, 2 M urea, 2 mM DTT, 25 mM Tris, pH 8.4).
   i) The suspension is centrifuged (40000×g, 15 minutes, 4° C.), the supernatant is discarded and the sediment is resuspended in 20 mL TBS by ultrasound treatment (150 mM NaCl, 0.5 mM PMSF, 20 mM Tris, pH 7.5).
   j) The suspension is centrifuged (40000×g, 15 minutes, 4° C.), the supernatant is discarded and the sediment is resuspended in a 10 mL denaturation solution by ultrasound treatment (8 M urea, 50 mM 4-(2-hydroxyethyl)-1-piperazineethanesulfonic acid (HEPES), 100 μM β-mercaptoethanol, pH 6.5) by ultrasound treatment and the suspension is incubated during 48 hours at 4° C. under slight shaking conditions.
   k) The suspension is centrifuged (40000×g, 15 minutes, 4° C.). The sediment is discarded and the centrifugation is repeated. The sediment is again discarded and the clear solution is filtered through a 0.22 μm filter, aliquoted and stored at −20° C. until further use. The protein concentration is determined by measuring the extinction at 280 nm in water. The extinction coefficient c of a class I molecule in these conditions is approximately 85000 M$^{-1}$ cm$^{-1}$.
   l) In the manner described here, the heavy subunit of the MHC class I and the light subunit (beta-2 microglobulin, β$_2$m) are either produced in two separate attempts (and subsequently mixed during refolding) or a fusion protein of the heavy and the light chain is correspondingly produced as a single protein.

4) Refolding the Class I Protein
   a) One liter refolding buffer (100 mM Tris-Cl pH 8.0, 0.5 M Arginine, 2 mM EDTA, 0.5 oxidized glutathione, 5 mM reduced glutathione) is mixed drop by drop while stirring at 4° C. with either 10 mg of denatured β$_2$m and 30 mg of denatured heavy subunit or with 20 mg of a fusion protein of the heavy and the light chain in a denaturing solution. The solution is stirred for another 12 hours.
   b) The solution is concentrated in a pressure filtration apparatus to approximately 100 ml and then in a centrifugal concentration apparatus (separation limit: 30000 Da) to approximately 1 ml and then centrifuged (16000×g, 4° C., 15 min); the sediment is discarded.
   c) The supernatant is filtered (0.22.mu.m) and applied on a gel filtration column (for example, GE Healthcare HiLoad™ 16/60 SUPERDEX® 75 prep grade) equilibrated in TBS (150 mM NaCl, 25 mM Tris-Cl, pH 7.5). The peak of the refolded class I molecule is identified by analysis of the samples with SDS-polyacrylamide gel electrophoresis: it contains heavy as well as light chains and has an apparent molecular weight of approximately 60000 Da.
   d) The corresponding fractions are united. The protein concentration is determined in the same way as above.

5) Production of a Class I Tetramer
  a) Refolded class I proteins are received in a biotinylation buffer (50 mM Tris-Cl pH 7.4; 150 mM NaCl; 1 mM biotin; 5 mM adenosine triphosphate; 5 mM $MgCl_2$) in a concentration of 5 μM and is mixed with 0.1 μM of recombinant BirA-biotinylation enzyme. The reaction is incubated during 12 hours at 25° C.
  b) The tetramerization is induced by adding 20 μM of fluorescent-marked avidin or streptavidin (for example, phycoerythrin-UltraAvidin™, Leinco), and the reaction is incubated for 15 min at 4° C.
  c) The tetramer complexes are cleaned by gel filtration with a SUPERDEX® S-200 column (equilibrated in TBS (25 mM Tris-Cl pH 7.4; 150 mM NaCl)).
  d) The corresponding fractions are united. The protein concentration is determined as described above.
6) Adding the Peptide
  a) In order to obtain a peptide-bonded tetramer, a solution of the tetramer in TBS is mixed with 10 μM of the corresponding peptide. The reaction is incubated for 15 min at 25° C.
  b) If necessary, the peptide tetramer complexes are cleaned by gel filtration with a Superdex® S-200 column (equilibrated in TBS). The corresponding fractions are united. The protein concentration is determined as described above.
7) Reaction of the Tetramer with T-Cells and Cytofluorometry
  SUPERDEX® S-200 column (equilibrated in TBS). The corresponding fractions are united. The protein concentration is determined as described above.
  b) The cells are centrifuged (800×g, 5 minutes, 4° C.) and the supernatant is removed. The cells are washed two times with FACS buffer and subsequently resuspended in fixation buffer (PBS, 2% paraformaldehyde).
  c) Cytofluorometry occurs with a commercially available apparatus (for example BectonDickinson FACSAria).

The present invention is not limited to embodiments described herein; reference should be had to the appended claims.

What is claimed is:

1. A protein produced by an expression system comprising a nucleic acid sequence that encodes an MHC class I heavy chain,
   wherein,
   the MHC class I heavy chain comprises an alpha-1 helix and an alpha-2 helix,
   the nucleic acid sequence has a disulfide bridge formed between the alpha-1 helix and the alpha-2 helix in the MHC class I heavy chain,
   the amino acid 139 is substituted by a cysteine so as to provide Cys-139,
   the amino acid 84 is substituted by the cysteine so as to provide Cys-84 or the amino acid 85 is substituted by the cysteine so as to provide Cys-85,
   the disulfide bridge is formed between the alpha-1 helix and the alpha-2 helix in the MHC class I heavy chain between Cys-139 and Cys-84 or between Cys-139 and Cys-85, and
   the protein comprises an anchor element selected from a natural biotinylation sequence, a polyhistidine sequence, or a polyarginine sequence.

2. A protein conjugate comprising the protein as recited in claim 1 and a marker that is a fluorescent colorant.

3. An MHC class I multimer comprising at least two proteins, wherein at least one of the at least two proteins is the protein as recited in claim 1.

4. The MHC class I multimer as recited in claim 3, wherein the multimer is a tetramer or a pentamer.

5. The MHC class I multimer as recited in claim 3, wherein the multimer comprises a marker disposed on the multimer, the marker being a fluorescent colorant.

6. The MHC class I multimer as recited in claim 3, wherein the multimer comprises an anchor element selected from a biotin molecule, a polyhistidine sequence, or a polyarginine sequence.

7. A reagent comprising:
   at least one of the protein as recited in claim 1 and the MHC class I multimer as recited in claim 3; and
   a peptide capable of binding to an MHC class 1 complex comprising said MHC class I heavy chain.

8. A kit for analyzing a T-cell frequency, the kit comprising:
   a first storage means comprising at least one of the protein as recited in claim 1 and the multimer as recited in claim 3; and
   a second storage means comprising a peptide capable of binding to an MHC class 1 complex comprising said MHC class I heavy chain,
   wherein a contents of the first storage means and the second storage means are configured to be combined.

9. A protein conjugate comprising the protein as recited in claim 1 and a marker, wherein the marker is a fluorescent colorant or a biotin molecule.

* * * * *